(12) United States Patent
Baker, Jr. et al.

(10) Patent No.: US 8,801,619 B2
(45) Date of Patent: Aug. 12, 2014

(54) PHOTOPLETHYSMOGRAPHY FOR DETERMINING VENTILATION WEANING READINESS

(75) Inventors: Clark R. Baker, Jr., Newman, CA (US); Shannon Campbell, Boulder, CO (US)

(73) Assignee: Covidien LP, Mansfield, MA (US)

( * ) Notice: Subject to any disclaimer, the term of this patent is extended or adjusted under 35 U.S.C. 154(b) by 337 days.

(21) Appl. No.: 13/174,421

(22) Filed: Jun. 30, 2011

(65) Prior Publication Data
US 2013/0006075 A1   Jan. 3, 2013

(51) Int. Cl.
*A61B 5/02* (2006.01)
*F16K 31/02* (2006.01)

(52) U.S. Cl.
USPC ........................ 600/483; 128/204.23

(58) Field of Classification Search
USPC ............... 600/529–543; 128/204.18, 204.23, 128/204.21
See application file for complete search history.

(56) References Cited

U.S. PATENT DOCUMENTS

| | | | |
|---|---|---|---|
| 5,355,880 A | 10/1994 | Thomas et al. | |
| 5,630,413 A | 5/1997 | Thomas et al. | |
| 6,662,032 B1* | 12/2003 | Gavish et al. | 600/323 |
| 7,246,618 B2 | 7/2007 | Habashi | |
| 7,425,201 B2 | 9/2008 | Euliano et al. | |
| 2005/0109340 A1 | 5/2005 | Tehrani | |
| 2005/0159987 A1* | 7/2005 | Rosenfeld et al. | 705/3 |
| 2005/0205093 A1 | 9/2005 | Jabour | |
| 2007/0000494 A1* | 1/2007 | Banner et al. | 128/204.23 |
| 2007/0232951 A1 | 10/2007 | Euliano et al. | |
| 2007/0282212 A1 | 12/2007 | Sierra et al. | |
| 2008/0156328 A1 | 7/2008 | Taub | |
| 2008/0183057 A1 | 7/2008 | Taub | |
| 2008/0236582 A1* | 10/2008 | Tehrani | 128/204.22 |
| 2008/0295839 A1 | 12/2008 | Habashi | |
| 2009/0229611 A1 | 9/2009 | Martin et al. | |
| 2010/0331724 A1 | 12/2010 | Watson et al. | |
| 2011/0021892 A1 | 1/2011 | Addison | |
| 2011/0071406 A1 | 3/2011 | Addison | |

FOREIGN PATENT DOCUMENTS

| | | |
|---|---|---|
| EP | 1740095 | 1/2007 |
| WO | WO2005096931 | 10/2005 |

OTHER PUBLICATIONS

U.S. Appl. No. 12/955,187, filed Nov. 29, 2010, Thomas A. Wilke.
Modawal, A. et al., "Weaning Success Among Ventilator-Dependant Patients in a Rehabilitation Facility", Arch Phys Med Rehabil 2002; 83(2): 154-57.
Esteban, A. et al., "Characteristics and Outcomes in Adult Patients Receiving Mechanical Ventilation, A 28-Day International Study", Caring for the Critically Ill Patient, JAMA 2002; 287(3): 345-355.

(Continued)

*Primary Examiner* — Michael D'Angelo
*Assistant Examiner* — Tiffany Weston
(74) *Attorney, Agent, or Firm* — Fletcher Yoder PC

(57) ABSTRACT

Embodiments of the present disclosure relate to a system and method for determining a likelihood of successful ventilator weaning for a patient undergoing mechanical or assisted ventilation. Specifically, embodiments provided herein include methods and systems for determining or predicting weaning readiness in a patient based on physiological parameters determined via photoplethysmography.

20 Claims, 5 Drawing Sheets

(56) References Cited

OTHER PUBLICATIONS

Orini, M. et al., "Time-Frequency Analysis of Cardiac and Respiratory Parameters for the Prediction of Ventilator Weaning", 30$^{th}$ Annual International IEEE EMBS Conf. Proc IEEE Eng. Med Biol Soc 2008; 2008:2793-2796.

Casaseca-De-La-Higuera, P. et al., "A Multichannel Model-Based Methodology for Extubation Readiness Decision of Patients on Weaning Trials"; IEEE Trans Biomed Eng 2009; 56(7):1849--1863.

* cited by examiner

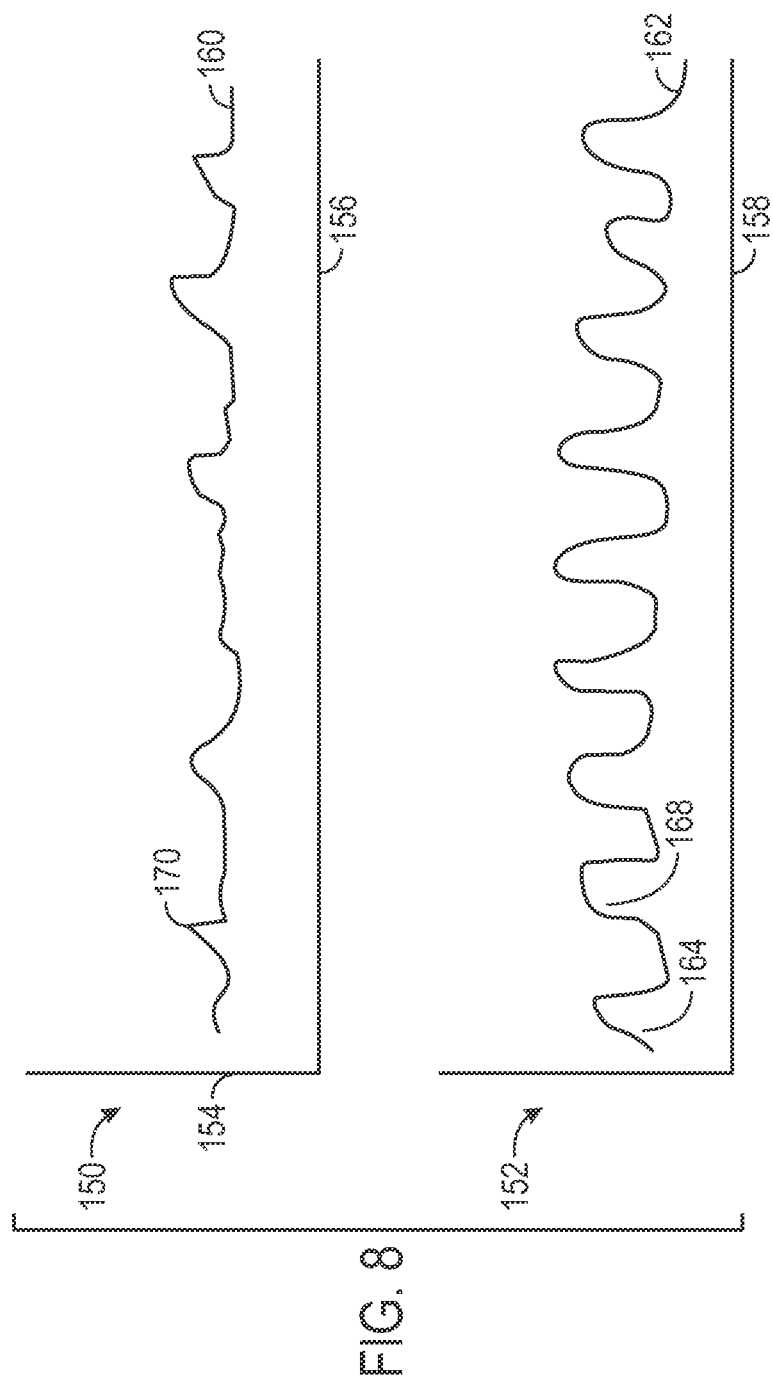

PHOTOPLETHYSMOGRAPHY FOR DETERMINING VENTILATION WEANING READINESS

BACKGROUND

The present disclosure relates generally to a method and system for monitoring physiological parameters of a patient. Specifically, embodiments of the present disclosure relate to estimation of certain clinical parameters, such as weaning readiness, by evaluating one or more parameters determined by photoplethysmography systems.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such characteristics of a patient. Such devices provide doctors and other healthcare personnel with the information they need to provide the best possible healthcare for their patients. As a result, such monitoring devices have become an indispensable part of modern medicine.

In the course of treating a patient, a tracheal tube (e.g., endotracheal, nasotracheal, or transtracheal device) may be used to control the flow of gases into the trachea of a patient. Often, a seal between the outside of the tube and the interior wall of the tracheal lumen is required, allowing for generation of positive intrathoracic pressure distal to the seal and prevention of ingress of solid or liquid matter into the lungs from proximal to the seal. In particular, tracheal tubes may be used over the course of weeks or months to ventilate a patient.

As a patient's clinical condition improves, a clinician may wish to remove the tracheal tube so that the patient can breathe independently. However, the determination of whether a patient is ready to be weaned from a ventilator is often a subjective process. That is, the clinician typically exercises professional judgment based on previous experience and an overall sense of how the patient is progressing. However, for some patients, weaning may fail because the patient is not strong enough to breathe without assistance, and the patient may require reintubation. Because removal and reinsertion of a tracheal tube may involve additional discomfort for the patient, it is desirable to more accurately determine if an intubated patient is ready to be weaned from a ventilator.

BRIEF DESCRIPTION OF THE DRAWINGS

Advantages of the disclosed techniques may become apparent upon reading the following detailed description and upon reference to the drawings in which:

FIG. 8 is a plot of an example of respiration rate variability trend for a patient.

DETAILED DESCRIPTION OF SPECIFIC EMBODIMENTS

Figure 1:
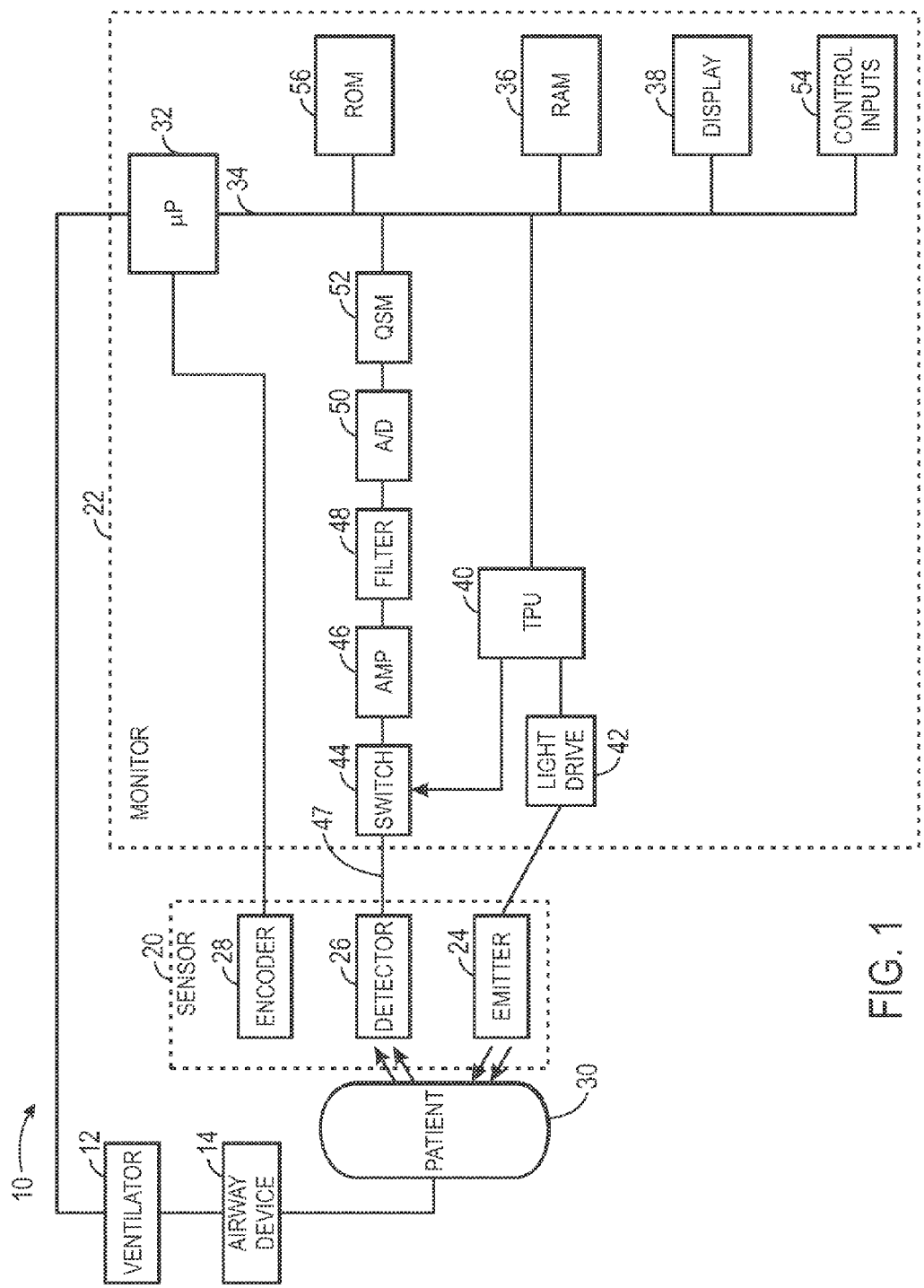
FIG. 1 is a block diagram of a patient monitor for determining weaning readiness in accordance with an embodiment.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Mechanical ventilation is used to provide breathing support for patients in emergency medical situations as well for patients with long-term medical needs. For patients treated with long-term breathing assistance, discontinuing the ventilation is a critical step in the recovery process. Accordingly, after observation of a patient's general clinical condition, clinicians may attempt weaning trials (e.g., 30 minutes of observation) in which the level of ventilation assistance is reduced as the patient's own breathing muscles are called upon to take over more and more of the breathing effort. Based on the volume and flow of respiratory gases (e.g., as assessed by the ventilator) during such partially-assisted breathing, the clinician may continue the weaning process and eventually extubate the patient. For some patients, breathing muscles tend to atrophy at a higher rate than other skeletal muscles. Because breathing muscle strength is difficult to assess directly and certain types of clinical conditions may not be evident during shorter observation periods, a patient may pass a weaning trial without being ready to be weaned. Such a patient may have insufficient muscle strength to take over from the ventilator and, after muscle exhaustion, may breathe rapidly and shallowly to compensate for weakened muscles. Because it is tiring for the patient to breathe rapidly and shallowly, this may eventually result in reintubation. Accordingly, it is desirable for clinicians to accurately determine if a patient is a candidate for ventilation weaning to prevent premature weaning.

Provided herein are techniques for determining weaning readiness of a ventilated patient by photoplethysmography. Photoplethysmography sensors are noninvasive optical sensors that may be used to emit light into a patient's tissue and detect the light that has passed through the tissue. Changes in the absorption of the light may be correlated to clinical parameters. In particular, photoplethysmography signals, such as those acquired by an optical sensor, may be used to calculate parameters affected by respiration that in turn may be used assess or predict a patient's ventilation weaning response. The photoplethysmography signal exhibits characteristic changes during respiration as a result of intrathoracic pressure changes and venous return resulting from the pressure exerted by breathing. These changes during respiration are translated to parameters that are calculated from the signal. The amount by which the parameters change may be indicative of the patient or ventilator effort (work of breathing) associated with of the respiration. Suitable parameters derived from a photoplethysmography signal for determining weaning readiness include heart rate, respiration rate, and oxygen saturation. Depending on a patient's particular clinical situation, additional plethysmographically-derived parameters affected by respiration may include the pulse amplitude, pulse frequency or pulse rate, pulse transit time, as well as modulation of the detected light level that may occur at the respiration rate due to changes in local blood volume at the plethysmography sensor site. Further, these plethysmographically-derived metrics may be used as surrogates for a patient's autonomic tone. Because respiration is controlled by the autonomic nervous system, low autonomic tone may be associated with a poor weaning prognosis.

In certain embodiments, the photoplethysmographically-derived parameters may be compared to a clinically-determined threshold to determine the weaning readiness. For example, based on the measured parameters, a patient undergoing ventilation weaning whose heart rate or respiration rate (or other parameter correlated to respiration) is above a clinically determined threshold may be considered to be in weaning failure. The clinician may then stop the weaning progress or may change the ventilation parameters to provide more breathing support for the patient. Similarly, measured values below a threshold may be correlated to weaning success. In other embodiments, changes in a patient's own measured parameters are used to determine weaning readiness. For example, in one embodiment, a baseline respiration state for the patient may be determined. Based on changes in the measured parameters relative to the baseline respiration state, the clinician may assess whether the patient is getting stronger and is ready to begin or progress with weaning. In other embodiments, the variability of a patient's plethysmographically-derived parameters may be calculated. In such embodiments, the variability may be used as a marker for weaning readiness. For example, a desired degree of variability for a particular parameter may be indicative of patient stability and weaning readiness.

The photoplethysmography information may be acquired by any suitable patient monitoring system. For example, FIG. 1 is a block diagram of a system 10 that may be configured to implement the embodiments of the present disclosure. As depicted, the system 10 may be used in conjunction with a patient receiving mechanical ventilation assistance from a ventilator 12 coupled to an airway apparatus 14 (e.g., a tracheal tube). Such a patient may also be monitored with a photoplethysmography sensor 20 coupled to a monitor 22. Suitable sensors include pulse oximetry sensors compatible with the Nellcor™ N-600x™ pulse oximetry monitor, such as an OxiMax™ sensor. The sensor 20 includes optical components such as a light emitter (e.g., a light emitting diode) and a light detector (e.g., a photodetector) that are applied to a patient and may be used to generate a plethysmographic waveform, which may be further processed by the monitor 22. The sensor 20 may be coupled to the monitor 22 wirelessly, or via a cable. The monitor 22 may include a microprocessor 32 coupled to an internal bus 34. Also connected to the bus 34 may be a RAM memory 36, a display 38, and controls inputs 54.

A time processing unit (TPU) 40 may provide timing control signals to light drive circuitry 42, which controls when the optical components of the optical sensor (e.g., photoplethysmography sensor 20) is activated, and, if multiple light sources are used, the multiplexed timing for the different light sources. In certain embodiments, the TPU 40 may also be used to synchronize information from the ventilator 12 and the sensor 20. The TPU 40 may also control the gating-in of signals from sensor 20 through a switching circuit 44. These signals are sampled at the proper time, depending at least in part upon which of multiple light sources is activated, if multiple light sources are used. The received signal from the sensor 20 may be passed through an amplifier 46, a low pass filter 48, and an analog-to-digital converter 50. The digital data may then be stored in a queued serial module (QSM) 52, for later downloading to RAM 36 or ROM 56 as QSM 52 fills up.

The emitter 24 may be capable of emitting one or more wavelengths of light, e.g., red and infrared (IR) light suitable for $SpO_2$ and pulse rate measurements, into the tissue of a patient 30, where the red wavelength may be between about 600 nm and about 700 nm, and the IR wavelength may be between about 800 nm and about 1000 nm. In other embodiments in which the sensor 20 is not used for pulse oximetry, the emitter 24 may emit a single wavelength of light that may be used to calculate the heart rate, respiration rate, or other relevant clinical parameters from a plethysmograph. The emitter 24 may include a single emitting device, for example, with one or more light emitting diodes (LEDs) or the emitter 24 may include a plurality of emitting devices with, for example, multiple LED's at various locations. Regardless of the number of light emitting devices, the emitter 24 may be used to measure, for example, blood oxygen saturation, water fractions, hematocrit, and/or other physiologic parameters of the patient, as discussed herein. It should be understood that, as used herein, the term "light" may refer to one or more of radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use in accordance with the present disclosure.

In one embodiment, the detector 26 may be an array of detector elements that may be capable of detecting light at various intensities and wavelengths. In operation, light enters the detector 26 after passing through the tissue of the patient. The detector 26 may then convert the light at a given intensity, which may be directly related to the absorbance and/or reflectance of light in the tissue of the patient, into an electrical signal. That is, when more light at a certain wavelength is absorbed or reflected, less light of that wavelength is typically received from the tissue by the detector 26. For example, the detector 26 may include one or more photodiodes, or any other element capable of converting light into either a current or voltage. After converting the received light to an electrical signal, the detector 26 may send the signal, which may be a plethysmographic ("pleth") signal, to the monitor 22, where physiological characteristics may be calculated based at least in part on the absorption of light in the tissue of the patient.

In some embodiments, the sensor 20 may include an encoder 28, which may contain information about the sensor 20, such as what type of sensor it is (e.g., whether the sensor is intended for placement on a forehead or digit) and the wavelengths of light emitted by the emitter 24. Further, the encoder 28 may contain information about dividing specific physiological characteristics (e.g., respiration rate and/or blood pressure) into tiers for monitoring and alarm threshold and sensitivity levels associated with those tiers. This information may allow the monitor 22 to select appropriate algorithms and/or calibration coefficients for calculating the patient's physiological characteristics. The encoder 28 may, for instance, be a memory on which one or more of the following information may be stored for communication to the monitor 22: the type of the sensor 20; the wavelengths of light emitted by the emitter 24; the proper calibration coefficients and/or algorithms to be used for calculating the patient's physiological characteristics, and monitoring tiers for physiological characteristics (e.g., respiration rate and/or blood pressure) and/or alarm threshold and sensitivity levels associated with those tiers. In one embodiment, the data or signal from the encoder 28 may be decoded by a decoder in the monitor 22.

Based at least in part upon the received signals corresponding to the light received by optical components of the sensor 20, microprocessor 32 may calculate parameters using suitable algorithms. In embodiments in which the weaning readiness is based at least in part on the heart rate, oxygen saturation, and/or pulse amplitude of the patient, these parameters may be determined by algorithms such as those employed by the Nellcor™ N-600x™ pulse oximetry monitor. In addition, in particular embodiments, the photoplethysmography sensor 20 may be a Nellcor™ pulse oximetry sensor, such as an OxiMax™ sensor. In addition, the microprocessor 32 may calculate a heart rate variability using various methods, such as those provided herein. These algorithms may employ certain coefficients, which may be empirically determined, and may correspond to the wavelengths of light used. The algorithms and coefficients may be stored in a ROM 56 or other suitable computer-readable storage medium and accessed and operated according to microprocessor 32 instructions. In one embodiment, the correction coefficients may be provided as a lookup table.

In certain embodiments, the weaning readiness (e.g., the heart rate or respiration rate or the variabilities thereof) may be determined from parameters derived from plethysmographic waveform information. Respiration rate may be determined as provided in U.S. Patent Publication Nos. 2011/0071406, filed Sep. 21, 2009, 2010/0331724, Jun. 30, 2009, or 2011/0021892, filed Jul. 23, 2009, the disclosures of which are incorporated by reference in their entireties herein for all purposes. For example, a plethysmographic signal from a pulse oximetry sensor may be transformed (e.g., using a continuous wavelet transform) to generate a primary scalogram. The scale or range of scales at which a band may appear on the primary scalogram is related to the respiration rate. In one embodiment, the respiration rate may be determined by analyzing a ridge corresponding to a characteristic frequency selected from the band. Depending on the type of sensor 20 used, the respiration rate may be determined by transforming both the red and IR signals or by applying the transform to only one of the red or the IR signal, e.g., in a single wavelength embodiment. Further, insofar as multiple parameters may be used to determine weaning readiness, trends for heart rate and respiration rate may be correlated to one another to determine a confidence level for the weaning readiness determination. For example, an increase in respiration rate observed in synchrony with a decrease in oxygen saturation may be associated with the type of shallow, rapid breathing indicative of weaning failure.

Variability of a particular parameter, e.g., heart rate, may be determined by any suitable method for extracting variability information over a measurement window, such as those provided in U.S. Patent Publication No. 2012/0136226, filed Nov. 29, 2010. That is, a respiration rate or heart rate may have certain breath-to-breath or beat-to-beat variability as well as longer term variability trends. A plot of the variability over time may account for breath-to-breath or beat-to-beat differences. The variability of a plethysmographically-determined parameter may be determined at least in part by calculating time domain or frequency domain statistics from the data collected from the sensor 20, such as mean heart rate, respiration rate, pulse amplitude, etc., standard deviation of pulse intervals (SDNN), square root of mean squared difference of successive pulse intervals (RMSSD), and the proportion of pulse intervals that differ from the mean (pNN50). A variability index or other metric for providing an indication to a caregiver may be derived from one or more time domain or frequency domain statistics. In one embodiment, the variability is expressed as a standard deviation, e.g., from a beat-to-beat or breath-to-breath interval time. In other embodiments, the variability may be expressed as a standard deviation from a mean value, e.g., mean pulse amplitude. This value may be expressed as a raw numerical value (e.g., a time value), or may be provided as an index, for example by comparing the calculated variability to a threshold. Accordingly, depending on the threshold, the indicator may be scaled to standard deviation from the cutoff, where a low index value represents a variability within one standard deviation of a threshold and a higher index value represents a variability that is more than one or two standard deviations from a threshold. In a particular embodiment, the variability may be expressed as a variability fraction. In other embodiments, two or more statistical parameters may be combined. Confidence in the calculated index may be determined by a percentage of valid intervals (i.e., pulse intervals) in a particular data time window, by a determination of signal quality, or by correlation to another parameter.

Figure 2:
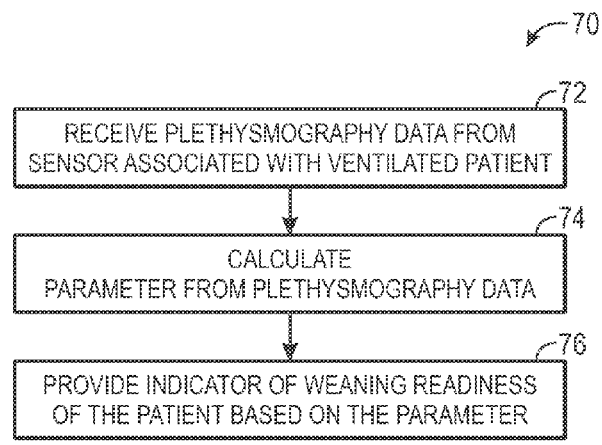
FIG. 2 is a flow diagram of a method for determining weaning readiness in accordance with an embodiment.

Regardless of the physiological parameter or combination of parameters employed by the system 10, the plethysmographically-derived parameters as provided change in a measurable manner during respiration depending on a patient's clinical condition. These changes may be measured and correlated to a patient's weaning readiness. FIG. 2 is a process flow diagram illustrating a method 70 for determining weaning readiness through evaluations of plethysmographically-determined parameters. The method may be performed as an automated procedure by a system, such as a system that includes a patient monitor 22 and a sensor 20. In addition, certain steps of the method may be performed by a processor, or a processor-based device such as a patient monitor 22 that includes instructions for implementing certain steps of the method 70. The weaning readiness may be assessed at any appropriate clinical state for the patient. In certain embodiments, the method 70 may be used to determine if a patient is ready for a weaning trial in which mechanical ventilation is decreased and the patient is given the opportunity to breathe on his own with also receiving some breathing assistance. In other embodiments, the method 70 may be used to determine if a patient undergoing a weaning trial is ready to be extubated.

The method 70 begins with receiving data from a photoplethysmography sensor 20 associated with a patient at step 72. The monitor 20 may calculate one or more physiological parameters from the photoplethysmography data at step 74. It should be understood that, in addition to heart rate and respiration rate, other plethysmographically-determined parameters may be used alone or in combination to determine a weaning readiness, including blood volume, pulse amplitude, pulse transit time, etc. After the physiological parameter has been determined, the parameter is evaluated to determine if its value is associated with weaning readiness and the patient is ready to undergo ventilatory weaning. To that end, an indicator or other marker of the weaning readiness of the patient based on the parameter and its relationship to respiration may be provided to a caregiver at step 76. For example, the monitor 22 may provide a display or other indication to a clinician, such as a graphical, visual, or audio representation of weaning readiness and/or the data from which the weaning readiness has been determined. A heart rate or oxygen saturation associated with weaning readiness may include a numeric value or a green light indicated on a display or a short tone generated by a speaker associated with monitor 22. Similarly, a heart rate or oxygen saturation associated with a patient not ready to be weaned may trigger another indicator or an alarm, which may include one or more of an audio or visual alarm indication. Further, for an extubated patient recently weaned from breathing support, the system 10 may provide an indicator or warning relating to weaning failure (e.g., high respiration rate, too high or too low respiration rate variability). Such a patient may be provided with breathing support and possibly reintubated. In particular embodiments, the indicator may be displayed along with a trend plot of the parameter from which the indicator was determined. (see FIGS. 3-4).

Figure 3:
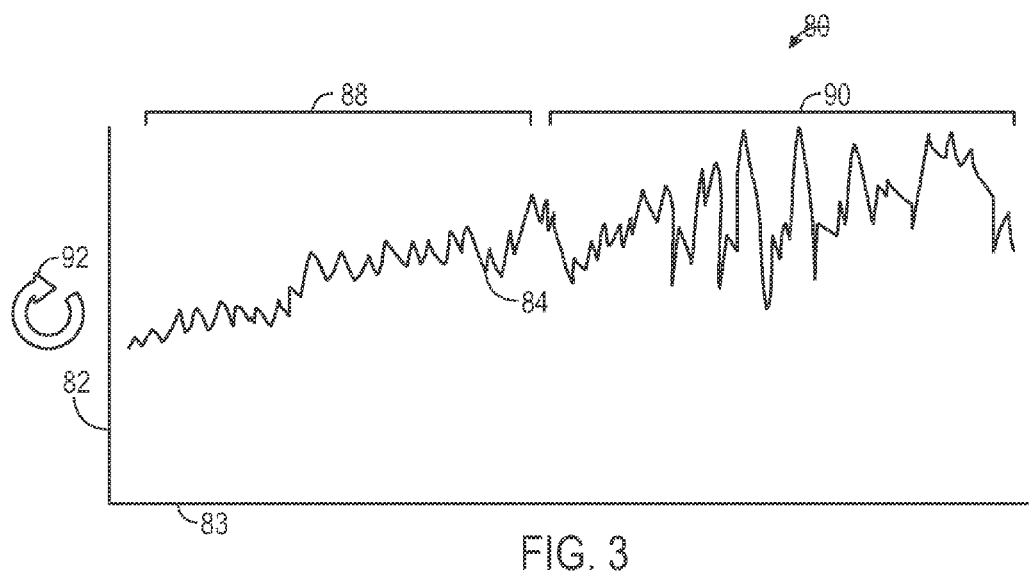
FIG. 3 is a plot of an example of heart rate trend for a patient.

As noted, the weaning readiness parameter may be evaluated over time so that a trend may be displayed and a variability of the parameter may be determined. As shown in FIG. 3, a heart rate, shown as example heart rate plot 80, may be plotted as the beats per minute on the y-axis 82 vs. time on the x-axis 83. As shown, the plotline 84 may be extrapolated from a series of data points. The collected data may be over a particular time period, such as five minutes, or may involve a threshold of beat-to-beat data points, such as 300 or more data points. The appropriate time for evaluating the heart rate may be dictated by the ventilator settings. For example, for a weaning trial of thirty minutes, the heart rate may be followed for the duration of the weaning trial. The heart rate may be evaluated for one or more characteristics, including the actual heart rate value, a heart rate trend, a heart rate variability, and a heart rate variability trend. Elevated heart rate may be correlated to respiratory distress and may be an indication of weaning failure. In other embodiments, a patient with a desired heart rate may not yet be ready to undergo weaning because of heart rate variability below of a desired threshold. In one embodiment, a heart rate variability value greater than 50 milliseconds (ms) or 75 ms may be considered to be associated with a good weaning prognosis, i.e., weaning readiness. In contrast, lower heart rate variability, which correlates to decreased autonomic nervous system function, may point to a lack of weaning readiness. In particular, a patient who is not ready to be weaned may exhibit a higher-than-normal heart rate and a low heart rate variability.

The plot 80 shows a hypothetical patient with a desired variability (e.g., beat-to-beat variability). Time window 88 is indicative of an overall upward trend in heart rate, and time window 90 indicative of an overall higher heart rate variability. Based on the trend data, the heart rate variability trend may also be determined. For the depicted embodiment, the variability may be increasing. In one embodiment, weaning readiness may be associated with a heart rate variability value that is substantially more than a predetermined value or within a predetermined range (e.g., within a standard deviation). For this patient, the trend towards increasing heart rate variability may be an overwhelming indicator that points towards a lack of weaning readiness. Further, an upward drift in heart rate may also be indicative of a lack of weaning readiness. As such, a displayed weaning indicator 92 may be red or otherwise indicate a lack of weaning readiness.

Figure 4:
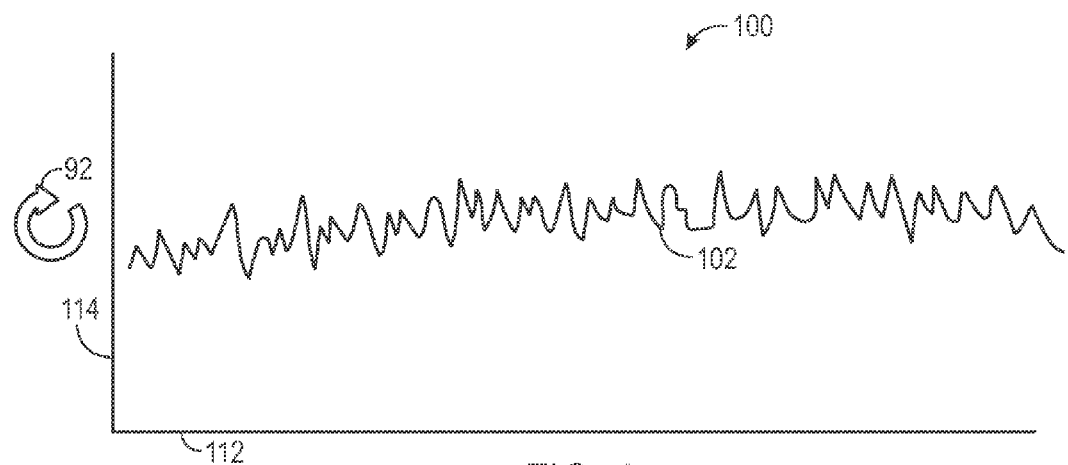
FIG. 4 is a plot of an example of heart rate trend for a patient.

A lack of upward or downward drift in a particular parameter may be associated with weaning readiness. FIG. 4 shows a plot 100 that may be indicative of a patient who may ready to undergo weaning (e.g., a weaning trial or extubation after a positive result for a weaning trial). Plotline 102 of a hypothetical patient is generally flat, indicating a lack of upward or downward drift of the heart rate. Further, the plotline 102 shows a desired beat-to-beat variability. In embodiments in which the variability is plotted, rather than the individual heart rate or other parameter values, the overall plotline for a patient who is ready to be weaned may be a generally flat trend line. Here, weaning indicator 92 may be green to indicate positive weaning readiness.

Figure 5:
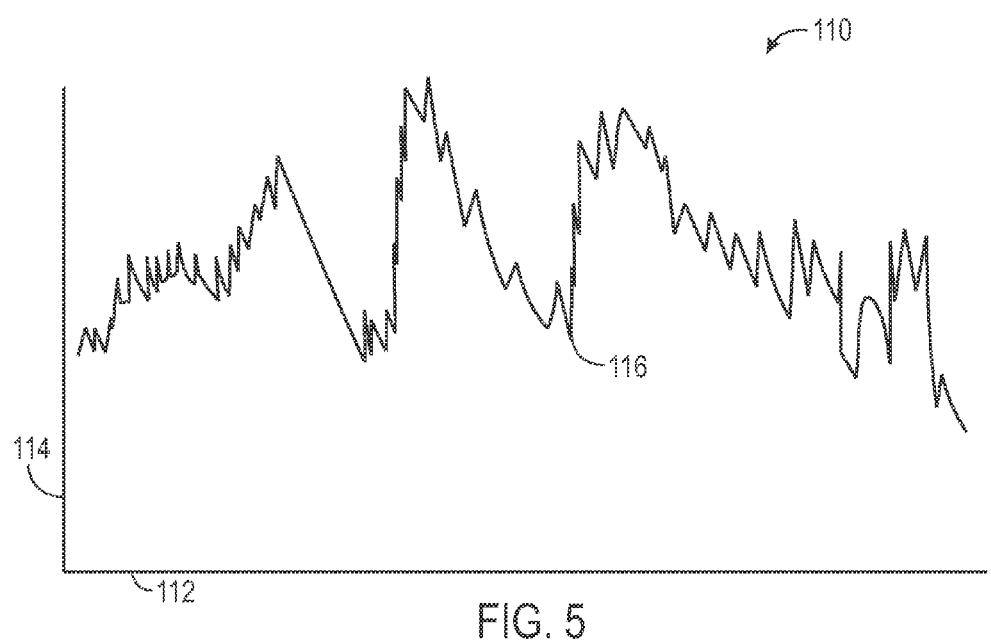
FIG. 5 is a plot of an example of respiration rate trend for a patient.

As noted, in addition to heart rate, respiration rate or other parameters may be used to determine weaning readiness. FIG. 5 is a plot 110 of respiration rate for a hypothetical patient. The plot 110 shows the respiration rate trend 116 over time on the x-axis 112 vs. the respiration rate in breaths per minute on the y-axis 114. Here, the overall trend shows overall high variability. Such variability may be associated with a lack of weaning readiness. A patient with strong autonomic nervous system control may have less variability in respiration rate, indicating appropriate breathing muscle activation.

Figure 6:
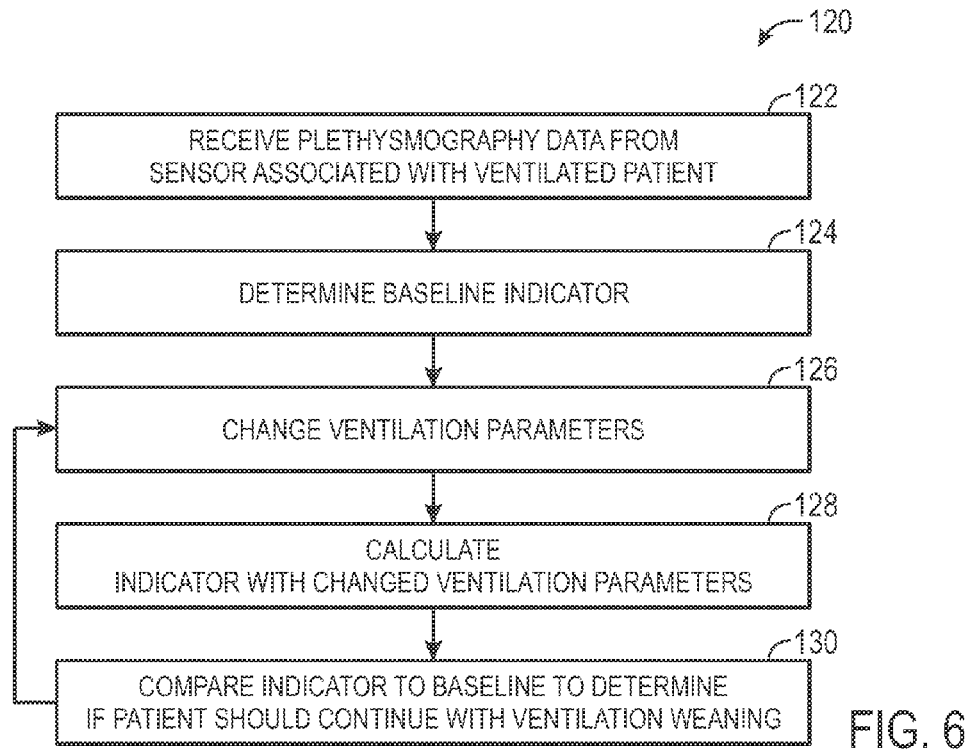
FIG. 6 is a flow diagram of an alternative method for determining weaning readiness in accordance with an embodiment.

In other embodiments, weaning readiness may be determined in the context of a patient's own baseline parameters. For instance, FIG. 6 depicts an embodiment of a method 120 for monitoring weaning readiness. In general, the method 120 may begin by receiving plethysmographic data from the sensor 20 at step 122. Upon the receipt of the data, the patient's baseline for one or more parameters may be determined at step 124. The monitor 22 may automatically establish a baseline within a set time window (e.g., 30 seconds). However, the caregiver may want to establish the baseline at a particular time or event (e.g., before or after starting a weaning trial at step 126). To do this the caregiver may manually input into the monitor 22 when to establish the baseline via the control inputs 56 provided on the monitor 22. For example, the monitor 22 may include an input for entering a baseline mode.

After baseline determination, the caregiver may adjust the ventilation parameters at step 126. For example, in one embodiment, the caregiver may reduce the pressure delivered by assist-control ventilation to start the ventilation weaning process. Assist-control is a commonly used mode of mechanical ventilation in medical intensive care units. In assist-control ventilation, the patient is able to trigger breaths. At the start of a cycle, the ventilator senses a patient's attempt at inhalation by detecting negative airway pressure or inspiratory flow. In assist-control the patient generally has a set minimum respiration rate. In assist-control mode, changes in the respiration rate may be tracked against ventilator delivered-breaths to account for the ventilator settings. In other embodiments, parameters such a heart rate or pulse amplitude may be used to determine the weaning readiness to account for the ventilator settings with regard to the respiration rate. In other embodiments, the ventilator settings, adjustments therein, and tracked changes in monitored parameters may be consistent with pressure support, tube compensation, proportional assist ventilation, or synchronized intermittent mandatory ventilation.

At step 128, the parameter is calculated and compared to the baseline at step 130. In the context of an intubated patient, full breathing support results in a respiration rate that is dictated by the ventilation settings and is selected to provide appropriate flow of gases to the lungs. As the patient takes over more of the breathing load, if the respiration rate is stable relative to baseline, the weaning may be progressing appropriately because the patient is not relying on shallow, rapid breaths that are associated with low autonomic tone or muscle weakness and the patient is able to offload at least some of the work of the ventilator. In other embodiments, a stable and high oxygen saturation during weaning may be indicative of weaning success because patient-triggered breaths are exhibiting appropriate oxygenation. On the other hand, an increase in respiration rate relative to baseline may be associated with weaning failure. In addition, a decrease in heart rate variability relative to baseline may be indicative of deterioration in autonomic tone and/or breathing muscle atrophy. Based on the comparison, a determination may be made if the weaning is progressing appropriately. If weaning is progressing appropriately and the calculated parameter is associated with weaning readiness, the method may return to step 126 to continue weaning and monitoring until the patient is fully weaned from the ventilator.

In certain embodiments, a particular parameter may have a characteristic shift from the exhaled portion of the breath cycle to the inspired portion. Depending on the magnitude of the shift, the weaning readiness may be determined. In one embodiment, a stronger patient (i.e., ready to be weaned) may have a relatively larger stroke volume, pulse pressure, pulse amplitude, and/or pulse rate during the inspiration portion of the breath cycle relative to the exhaled portion of the breath cycle. The same patient may have decreased intrathoracic pressure during the inspired portion of the breath. In contrast, a weaker patient (e.g., not ready to be weaned) may have decreased stroke volume, pulse pressure, pulse amplitude, and/or pulse rate during the inspiration portion of the breath cycle relative to the exhaled portion of the breath cycle. A patient that may benefit from additional monitoring before weaning decisions are made may have little variability between the inspired and exhaled portions of the breath. Such differences may be determined on a breath to breath basis or over a time window (e.g., inspire variability relative to exhale). In addition, the effect of these parameters may change based on the patient's ventilation characteristics. Inspiration via mechanical ventilation increases thoracic pressure while inspiration via patient effort decreases intrathoracic pressure. Further, the presence of an endotracheal tube increases the work required to move air through the airway, for a supported or patient-triggered breath. Such information may be taken into account by the system 10. For example, the system 10 may calibrate determinations of the parameters in question based on the presence of an endtroacheal tube. In addition, the system 10 may account for intrathoracic pressure differences between patient-triggered and mechanical breaths. In one embodiment, such factors may magnify the differences between a patient ready to be weaned (e.g., a patient whose breathing is partially supported) and a patient breathing without any support. Accordingly, the system 10 may account for the mechanical ventilation status of the patient in determining weaning readiness or success. Further, the size of any differences in intrathoracic pressure as a result of a change in ventilation status may be used as an additional factor in determining weaning success. That is, as the patient-triggered or unsupported breathing increases over the course of weaning, a concurrent relative drop in intrathoracic pressure may be an indicator of weaning success while a lack of such a relative drop may be an indicator of weaning failure or a signal to pause the weaning process until the patient is stronger.

Figure 7:
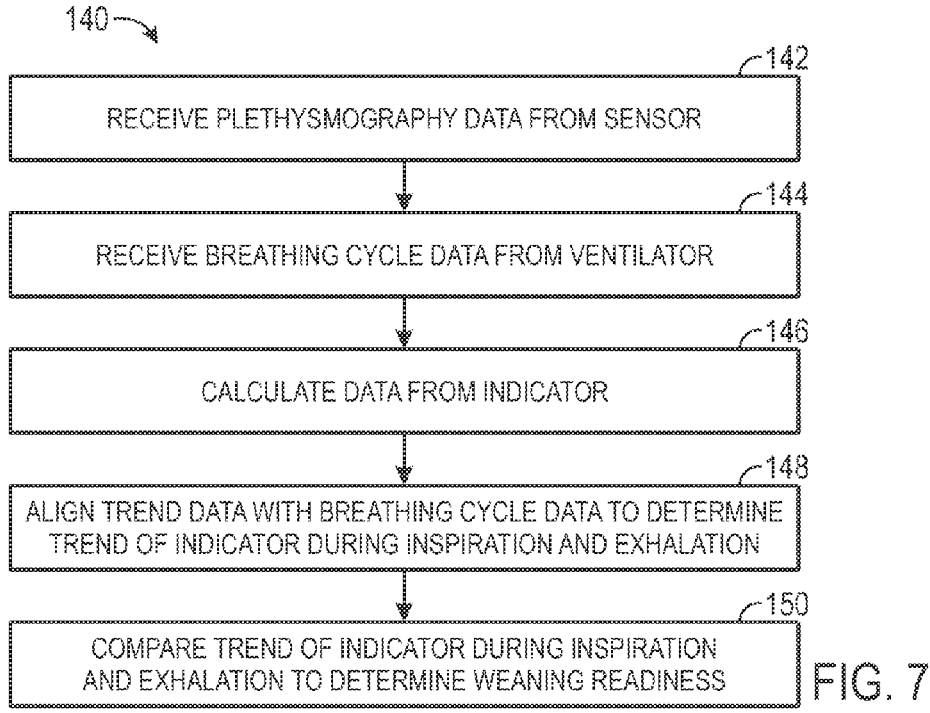
FIG. 7 is a flow diagram of a method for determining weaning readiness that includes ventilation information in accordance with an embodiment.

The system 10 as provided may integrate information from a ventilator 12 with the monitor 22 to align a patient's breath cycle with the plethysmographic monitoring information so that the parameters calculated during inspiration may be compared to parameters calculated during exhalation. FIG. 7 is a flow diagram of a method 140 for monitoring weaning readiness by comparing plethysmographically-derived parameters determined during inspiration and exhalation. The monitor 22 receives photoplethysmography data from the sensor 20 at step 142 and breathing cycle data from the ventilator 12 at step 144. For example, because the ventilator 14 controls the timing of the inhale and exhale portions of the breath, a signal may be sent to the monitor 22 with time stamp information for each portion of the breath cycle. At step 146, the monitor 22 calculates a trend of the appropriate plethysmographically-derived parameter related to autonomic tone (e.g., values or variabilities), and, after alignment of the trend data with the breathing cycle data at step 148, compares the parameter in the inspire portion of the breath to the parameter in the exhale portion of the breath.

FIG. 8 is an example of a display of respiration rate variability (plot 150) and breathing cycle data (shown as a $CO_2$ waveform plot 152) that may be evaluated and displayed by the monitor 22. The respiration rate variability is shown over time (x-axis 152) on the y-axis 156. The breathing cycle time axis 158 is aligned to the respiration rate variability time axis 156. In this manner, the respiration rate variability plotline 160 may be compared to the $CO_2$ waveform 162 that is indicative of the breathing cycle. For example, adjacent waves 164 and 168 may represent exhalation and inspiration portions of the breath cycle. The breathing cycle information may be compared to any variability on the respiration rate trend (e.g., increase 170) to determine if the patient is ready to be weaned. In the depicted example of the hypothetical patient, the respiration rate trend is generally unchanging, which may be indicative of weaning readiness. Likewise, a trend or variability plot may present one or more plethysmographically-derived metrics indicative of intrathoracic pressure variation or patient versus mechanical ventilator effort (e.g. beat-to-beat pulse amplitude or pulse period), aligned with the breathing cycle data in plot 152, as an indication of weaning readiness.

While the disclosure may be susceptible to various modifications and alternative forms, specific embodiments have been shown by way of example in the drawings and will be described in detail herein. However, it should be understood that the disclosure is not intended to be limited to the particular forms disclosed. Rather, the disclosure is to cover all modifications, equivalents and alternatives falling within the spirit and scope of the disclosure as defined by the following appended claims.

What is claimed is:

1. A monitor, comprising:
an input circuit configured to receive a photoplethysmography signal from a ventilated patient;
a memory storing an algorithm configured to determine one or more characteristics of the photoplethysmography signal indicative of a ventilation weaning readiness and to determine the ventilation weaning readiness of the ventilated patient based on the one or more characteristics, wherein the one or more characteristics comprise pulse amplitude, and wherein the algorithm is configured to determine weaning readiness based at least in part on an increase in pulse amplitude during an inspiration phase relative to an exhalation phase of a breathing cycle of the ventilated patient;
a processor configured to execute the algorithm; and
a display configured to provide an indication of the ventilation weaning readiness of the ventilated patient.

2. The monitor of claim 1, wherein the input circuit is configured to receive information related to the breathing cycle of the ventilated patient.

3. The monitor of claim 1, wherein the one or more characteristics of the photoplethysmography signal indicative of ventilation weaning readiness further comprises a pulse pressure, an intrathoracic pressure, a modulation of local blood volume at the ventilation rate, a stroke volume, a heart rate, a pulse transit time, or a combination thereof.

4. The monitor of claim 1, wherein the algorithm is configured to determine a lack of weaning readiness based at least in part on a decrease in pulse amplitude, pulse pressure, or heart rate during the inspiration phase relative to the exhalation phase.

5. The monitor of claim 1, wherein the one or more characteristics of the photoplethysmography signal indicative of ventilation weaning readiness further comprises a pulse amplitude variability, a pulse pressure variability, a modulation of local blood volume at the ventilation rate, a stroke volume variability, a heart rate variability, a pulse transit time, or combination thereof.

6. The monitor of claim 1, wherein the monitor comprises a weaning mode, wherein the algorithm is executed during the weaning mode and not executed when not in the weaning mode.

7. The monitor of claim 1, wherein the monitor comprises a baseline mode and wherein the algorithm is configured to determine a baseline characteristic of ventilation weaning readiness during the baseline mode.

8. A system for determining ventilation weaning readiness comprising:
a sensor configured to acquire photoplethysmography data from a ventilated patient and to generate a signal relating to the photoplethysmography data; and
a monitor configured to:
receive the signal;
determining a ventilation weaning readiness of the patient based at least in part on the signal; and
provide an indication of ventilation weaning readiness, wherein the indication of ventilation weaning readiness is based at least in part on an increased pulse amplitude during inspiration relative to exhalation.

9. The system of claim 8, wherein the indication of ventilation weaning readiness is based at least in part on an increased heart rate variability during inspiration relative to exhalation.

10. The monitor of claim 1, wherein the algorithm is configured to determine weaning readiness based at least in part on a comparison of the one or more characteristics to a clinically-determined threshold.

11. The monitor of claim 1, wherein providing an indication of weaning readiness comprises providing a graphical representation of weaning readiness.

12. The monitor of claim 7, wherein the monitor is configured to enter the baseline mode in response to a user input.

13. A system for determining ventilation weaning readiness, comprising:
a sensor configured to acquire photoplethysmography data from a ventilated patient and generate a signal relating to the photoplethysmography data; and
a monitor configured to:
receive the signal;
determine a ventilation weaning readiness of the patient based at least in part on the signal; and provide an indication of the ventilation weaning readiness, wherein the indication of ventilation weaning readiness is based at least in part on a correlation between pulse amplitude modulation and respiration rate.

14. The system of claim 13, wherein the indication of ventilation weaning readiness is based at least in part on an increased pulse amplitude during inspiration relative to exhalation.

15. A system for determining ventilation weaning readiness, comprising:
a sensor configured to acquire photoplethysmography data from a ventilated patient and generate a signal relating to the photoplethysmography data; and
a monitor configured to:
receive the signal;
determine a ventilation weaning readiness of the patient based at least in part on the signal; and
provide an indication of the ventilation weaning readiness, wherein the indication of ventilation weaning readiness is based at least in part on an increased heart rate during inspiration relative to exhalation.

16. A monitor, comprising:
an input circuit configured to receive a photoplethysmography signal from a ventilated patient;
a memory storing an algorithm configured to determine one or more characteristics of the photoplethysmography signal indicative of a ventilation weaning readiness and to determine the ventilation weaning readiness of the ventilated patient based on the one or more characteristics, wherein the one or more characteristics comprise pulse pressure, and wherein the algorithm is configured to determine weaning readiness based at least in part on an increase in pulse pressure during an inspiration phase relative to an exhalation phase of a breathing cycle of the ventilated patient;
a processor configured to execute the algorithm; and
a display configured to provide an indication of the ventilation weaning readiness of the ventilated patient.

17. The monitor of claim 16, wherein the algorithm is configured to determine a lack of weaning readiness based at least in part on a decrease in pulse amplitude, pulse pressure, or heart rate during the inspiration phase relative to the exhalation phase.

18. A monitor, comprising:
an input circuit configured to receive a photoplethysmography signal from a ventilated patient;
a memory storing an algorithm configured to determine one or more characteristics of the photoplethysmography signal indicative of a ventilation weaning readiness and to determine the ventilation weaning readiness of the ventilated patient based on the one or more characteristics, wherein the one or more characteristics comprise heart rate, and wherein the algorithm is configured to determine weaning readiness based at least in part on an increase in heart rate during an inspiration phase relative to an exhalation phase of a breathing cycle of the ventilated patient;
a processor configured to execute the algorithm; and
a display configured to provide an indication of the ventilation weaning readiness of the ventilated patient.

19. A monitor, comprising:
an input circuit configured to receive a photoplethysmography signal from a ventilated patient;
a memory storing an algorithm configured to determine one or more characteristics of the photoplethysmography signal indicative of a ventilation weaning readiness and to determine the ventilation weaning readiness of the ventilated patient based on the one or more characteristics, wherein the one or more characteristics comprise pulse amplitude modulation and respiration rate, and wherein the algorithm is configured to determine weaning readiness based at least in part on a correlation between pulse amplitude modulation and respiration rate;

a processor configured to execute the algorithm; and
a display configured to provide an indication of the ventilation weaning readiness of the ventilated patient.

20. A monitor, comprising:
   an input circuit configured to receive a photoplethysmography signal from a ventilated patient;
   a memory storing an algorithm configured to determine one or more characteristics of the photoplethysmography signal indicative of a ventilation weaning readiness and to determine the ventilation weaning readiness of the ventilated patient based on the one or more characteristics, wherein the one or more characteristics comprise heart rate variability, and wherein the algorithm is configured to determine weaning readiness based at least in part on an increase in heart rate variability during an inspiration phase relative to an exhalation phase of a breathing cycle of the ventilated patient;
   a processor configured to execute the algorithm; and
   a display configured to provide an indication of the ventilation weaning readiness of the ventilated patient.

* * * * *